United States Patent
Jhon et al.

(10) Patent No.: US 8,137,970 B2
(45) Date of Patent: Mar. 20, 2012

(54) METHODS FOR INDUCING THE DIFFERENTIATION OF HEMATOPOIETIC STEM CELLS INTO MEGAKARYOCYTES AND PLATELETS, AND GENE CONTROLLING THE DIFFERENTIATION

(75) Inventors: Gil-Ja Jhon, Seoul (KR); Jin-Kyung Limb, Seoul (KR); Yun Soo Bae, Gyeonggi-do (KR); Jae Sang Kim, Seoul (KR); Gyoon Hee Han, Gyeonggi-do (KR); So-Yeop Han, Seoul (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 117 days.

(21) Appl. No.: 12/364,341

(22) Filed: Feb. 2, 2009

(65) Prior Publication Data
US 2009/0324583 A1     Dec. 31, 2009

(30) Foreign Application Priority Data

Jun. 30, 2008   (KR) ........................ 10-2008-0062968
Jun. 30, 2008   (KR) ........................ 10-2008-0062969

(51) Int. Cl.
C12N 5/00     (2006.01)
C12N 5/08     (2006.01)
(52) U.S. Cl. ....................................................... 435/377
(58) Field of Classification Search ........................ None
See application file for complete search history.

(56)  References Cited

FOREIGN PATENT DOCUMENTS

| KR | 10-0688261 | | 2/2007 |
| KR | 1020070073932 A | | 7/2007 |
| WO | WO 2007/058497 | * | 5/2007 |

OTHER PUBLICATIONS

Whalen et al . Mol.Cell Biology, 1997, pp. 1947-1958.*

* cited by examiner

Primary Examiner — Michail Belyavskyi
(74) Attorney, Agent, or Firm — Seed IP Law Group PLLC

(57) ABSTRACT

The present invention relates to a method for inducing the differentiation of CD34+ hematopoietic stem cells into megakaryocytes and platelets, more particularly, a method for inducing the differentiation of CD34+ hematopoietic stem cells into megakaryocytes and platelets comprising the steps of coculturing CD34+ hematopoietic stem cells with stromal cells and adding the compound of Formula 1. Further, the present invention relates to a composition for detecting the differentiation of hematopoietic stem cells into megakaryocytes and platelets, comprising an agent measuring expression level of a gene that is selected from the group consisting of KLF2 (Kiruppel-like factor2), LOC138255 (OTTHUMP00000021439), GDF15 (growth differentiation factor 15) and INHBE (inhibin, betaE), a kit comprising the composition, a method for detecting the differentiation into megakaryocytes and platelets by using the marker genes, a method for regulating the differentiation into megakaryocytes and platelets, and a method for screening a candidate compound that regulates the differentiation into megakaryocytes and platelets.

3 Claims, 6 Drawing Sheets

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: forward primer for identifying KLF2 gene

<400> SEQUENCE: 1
gcaagaccta caccaagagt tcg                                            23
```

<210> SEQ ID NO 2
<211> LENGTH: 19
<212> TYPE: DNA
<213> ORGANISM: Artificial Sequence
<220> FEATURE:
<223> OTHER INFORMATION: reverse primer for identifying KLF2 gene

<400> SEQUENCE: 2
catgtgccgt ttcatgtgc                                               19

<210> SEQ ID NO 3
<211> LENGTH: 20
<212> TYPE: DNA
<213> ORGANISM: Artificial Sequence
<220> FEATURE:
<223> OTHER INFORMATION: forward primer for identifying LOC138255 gene

<400> SEQUENCE: 3
atgaggaaac agtgagctcc                                              20

<210> SEQ ID NO 4
<211> LENGTH: 20
<212> TYPE: DNA
<213> ORGANISM: Artificial Sequence
<220> FEATURE:
<223> OTHER INFORMATION: reverse primer for identifying LOC138255 gene

<400> SEQUENCE: 4
aatcccactc tcatcatgcc                                              20

<210> SEQ ID NO 5
<211> LENGTH: 20
<212> TYPE: DNA
<213> ORGANISM: Artificial Sequence
<220> FEATURE:
<223> OTHER INFORMATION: forward primer for identifying GDF15 gene

<400> SEQUENCE: 5
atggctctca gatgctcctg                                              20

<210> SEQ ID NO 6
<211> LENGTH: 20
<212> TYPE: DNA
<213> ORGANISM: Artificial Sequence
<220> FEATURE:
<223> OTHER INFORMATION: reverse primer for identifying GDF15 gene

<400> SEQUENCE: 6
agagatacgc aggtgcaggt                                              20

<210> SEQ ID NO 7
<211> LENGTH: 20
<212> TYPE: DNA
<213> ORGANISM: Artificial Sequence
<220> FEATURE:
<223> OTHER INFORMATION: forward primer for identifying INHBE gene

<400> SEQUENCE: 7
atgggttgca cctgaccagt                                              20

<210> SEQ ID NO 8
<211> LENGTH: 20
<212> TYPE: DNA
<213> ORGANISM: Artificial Sequence
<220> FEATURE:
<223> OTHER INFORMATION: reverse primer for identifying INHBE gene

```
<400> SEQUENCE: 8
ttggtgatgt ggtgctcagc                                               20

<210> SEQ ID NO 9
<211> LENGTH: 20
<212> TYPE: DNA
<213> ORGANISM: Artificial Sequence
<220> FEATURE:
<223> OTHER INFORMATION: forward primer for identifying GAPDH gene

<400> SEQUENCE: 9
ctgcaccacc aactgcttag                                               20

<210> SEQ ID NO 10
<211> LENGTH: 20
<212> TYPE: DNA
<213> ORGANISM: Artificial Sequence
<220> FEATURE:
<223> OTHER INFORMATION: reverse primer for identifying GAPDH gene

<400> SEQUENCE: 10
agatccacga cggacacatt                                               20
```

METHODS FOR INDUCING THE DIFFERENTIATION OF HEMATOPOIETIC STEM CELLS INTO MEGAKARYOCYTES AND PLATELETS, AND GENE CONTROLLING THE DIFFERENTIATION

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310160_401_SEQUENCE_LISTING.txt. The text file is 3 KB, was created on Apr. 27, 2009, and is being submitted electronically via EFS-Web.

BACKGROUND

1. Technical Field

The present invention relates to a method for inducing the differentiation of hematopoietic stem cells into megakaryocytes and platelets, a gene controlling the differentiation, and uses thereof.

2. Description of the Related Art

Platelets, playing a crucial role in hemostasis or blood coagulation, measure 2 to 3 μm in diameter, with a mean blood concentration of 300,000 to 500,000 cells/mm$^2$. They are sticky and viscous, and the morphology thereof varies depending on conditions. Platelets adhere and coagulate on damaged tissue and at the same time, release intracellular components which induce a series of coagulation reactions.

Thrombocytopoiesis is the process in which megakaryocytic progenitor cells derived from multipotent stem cells are transformed into megakaryocytes via megakaryoblasts and platelets are then produced from megakaryocytes. The studies of the regulation of megakaryocytopoiesis and thrombocytopoiesis have been carried out by Mazur (Exp. Hematol., 15:248, 1987) and Hoffman (Blood, 74:1196-1212, 1989). For example, bone marrow pluripotent stem cells are differentiated into megakaryocytes, erythrocytes, and myelocytes. Megaloblasts are among the megakaryocytic lineage cells detectable in the early stages of development. These cells have basophilic cytoplasms, reticular chromatin, and one morphologically irregular nucleus containing several nucleoli, and range in diameter from 20 to 30 μm. Within a short time, megakaryocytes have up to 32 nuclei (polyploidy) while the cytoplasm remains largely immature. With the advance of maturation, the nuclei undergo further lobulation and concentration while the cytoplasm increases in volume and is further acidophilic and granulated. In the most mature megakaryocytic lineage cells, platelets are observed to be released from cell verges. Generally, less than 10% of megakaryocytes are in an erythroblastic stage, while more than 50% undergo maturation. Typically, megakaryocytes are morphologically classified into early-stage progenitor megakaryocytes, mid-stage promegakaryocytes or basophilic megakaryocytes, and late-stage mature megakaryocytes (acidophilic, granulate and responsible for platelet biogenesis). Mature megakaryocytes shed cytoplasmic filaments into sinusoidal lumens wherein they are fragmented into individual platelets (Williams et al., Hematology, 1972).

Thrombocytopenia means a reduction in platelet count, caused by the destruction of megakaryocyte colony-forming units, which are the progenitor cells of megakaryocytes present in the bone marrow. Recently, there are several different forms of thrombocytopenia; hereditary thrombocytopenia, idiopathic thrombocytopenic purpura, and aplastic anemia. A clinically more important form of thrombocytopenia is secondary thrombocytopenia which is induced by general irradiation with X-rays, or by the administration of drugs which prevent hematopoiesis. In many cases, secondary thrombocytopenia is caused by chemotherapy, radiotherapy, bone marrow transplantation, or the like applied to cancer patients which results in inadequate formation of bone marrow megakaryocytes. Secondary thrombocytopenia is a dangerous disease which impedes the recovery of the patient and sometimes causes death by bleeding.

A therapy for thrombocytopenia which is currently most frequently used involves platelet transfusion in order to keep the platelet count at a value of more than 20,000/μl. However, it has problems that the donors of blood needed for platelet transfusion are lack, and the infection such as AIDS virus or hepatitis virus derived from blood and immune response according to foreign platelet transfusion occurs.

Therefore, there is a need for the development of substances capable of directly promoting thrombocytopoiesis, which may be directly administered to patients or to the pluripotent hematopoietic stem cells, leading to their differentiation into thrombocytes and an increase in the count.

In contrast, thrombocythemia is a chronic disorder associated with increased or abnormal production of blood platelets. Since platelets are involved in blood clotting, their abnormal production can result in the inappropriate formation of blood clots or in bleeding, with the consequence of an increased risk of gastrointestinal bleeding, heart attack and stroke. Examples of diseases associated with thrombocythemia include essential thrombocythemia (ET), chronic myelogenous (CML), polycythemia vera (PV), agnogenic mteloid metaplasia (AMM), and sickle cell anemia (SCA). To treat thrombocythemia, studies have been made on the compounds inhibiting the platelet production.

Stem cell possesses two properties of multipotency and self renewal, and is found in both embryonic and adult cells. Since one stem cell is able to differentiate into a specialized cell or organ, much interest has focused on organ transplantation or cell therapy using stem cells.

Such platelet-related diseases are caused by increased or decreased production of blood platelets through the specific mechanisms. Therefore, if the genes involved in differentiation of stem cells into megakaryocytes and platelets are used as a target gene for the treatment of thrombocytopenia or thrombocythemia, it is expected that platelet differentiation can be effectively controlled.

Accordingly, intensive and thorough research into thrombocytopoiesis, conducted by the present inventors, resulted in the finding that the compound of Formula 1 of the present invention is highly effective in inducing the differentiation of CD34 positive hematopoietic stem cells into megakaryocytes and thrombocytes. In addition, the present inventors have identified novel genes that are involved in the differentiation of hematopoietic stem cells into megakaryocytes and platelets. They found that the genes can substantially control the differentiation of hematopoietic stem cells into megakaryocytes and platelets, and thus the gene can be used as a target gene for the treatment of thrombocythemia and thrombocytopenia, and as a megakaryocyte/platelet differentiation marker, thereby completing the present invention.

BRIEF SUMMARY

It is an object of the present invention to provide a method for inducing the differentiation of hematopoietic stem cells into megakaryocytes and platelets, more particularly, a method for inducing the differentiation of hematopoietic stem cells into megakaryocytes and platelets, comprising the steps of (a) coculturing CD34+ hematopoietic stem cells with stromal cells; and (b) adding a compound of Formula 1, and a composition thereof.

It is another object of the present invention to provide a composition for detecting the differentiation of hematopoietic stem cells into megakaryocytes and platelets, comprising an agent measuring expression level of a gene that is selected from the group consisting of KLF2 (Kiruppel-like factor2), LOC138255 (OTTHUMP00000021439), GDF15 (growth differentiation factor 15) and INHBE (inhibin, betaE).

It is still another object of the present invention to provide a kit for detecting the differentiation marker from hematopoietic stem cells into megakaryocytes and platelets, comprising the composition.

It is still another object of the present invention to provide a method for detecting the differentiation of hematopoietic stem cells into megakaryocytes and platelets by examining expression levels of the genes.

It is still another object of the present invention to provide a differentiation regulator for regulating the differentiation of hematopoietic stem cells into megakaryocytes and platelets, comprising the genes as an effective ingredient.

It is still another object of the present invention to provide a method for regulating the differentiation of hematopoietic stem cells into megakaryocytes and platelets by increasing or decreasing expression of the genes.

It is still another object of the present invention to provide a pharmaceutical composition for the treatment of thrombocytopenia, comprising a gene expression- or protein activity-promoting material as an effective ingredient.

It is still another object of the present invention to provide a pharmaceutical composition for the treatment of thrombocytopenia, comprising a gene expression- or protein activity-inhibiting material as an effective ingredient.

It is still another object of the present invention to provide a method for screening a candidate compound that regulates the differentiation of hematopoietic stem cells into megakaryocytes and platelets, comprising the step of measuring an increase or decrease in expression levels of the marker genes.

It is still another object of the present invention to provide a therapeutic composition for thrombocythemia or thrombocytopenia, comprising the compound that regulates the differentiation of hematopoietic stem cells into megakaryocytes and platelets, selected by the screening method, as an effective ingredient.

As described above, the differentiation of CD34+ hematopoietic stem cells into megakaryocytes and platelets can be effectively induced by coculturing the CD34+ hematopoietic stem cells with stromal cells in the compound of Formula 1.

Further, the identified differentiation marker genes can be used as a marker capable of readily detecting the megakaryocyte/platelet differentiation for the treatment of thrombocytopenia. The marker genes can be also used as a target gene for regulating the differentiation of hematopoietic stem cells into megakaryocytes and platelets, or used to screen a candidate compound capable of regulating the differentiation of hematopoietic stem cells into megakaryocytes and platelets.

DETAILED DESCRIPTION

Figure 1:
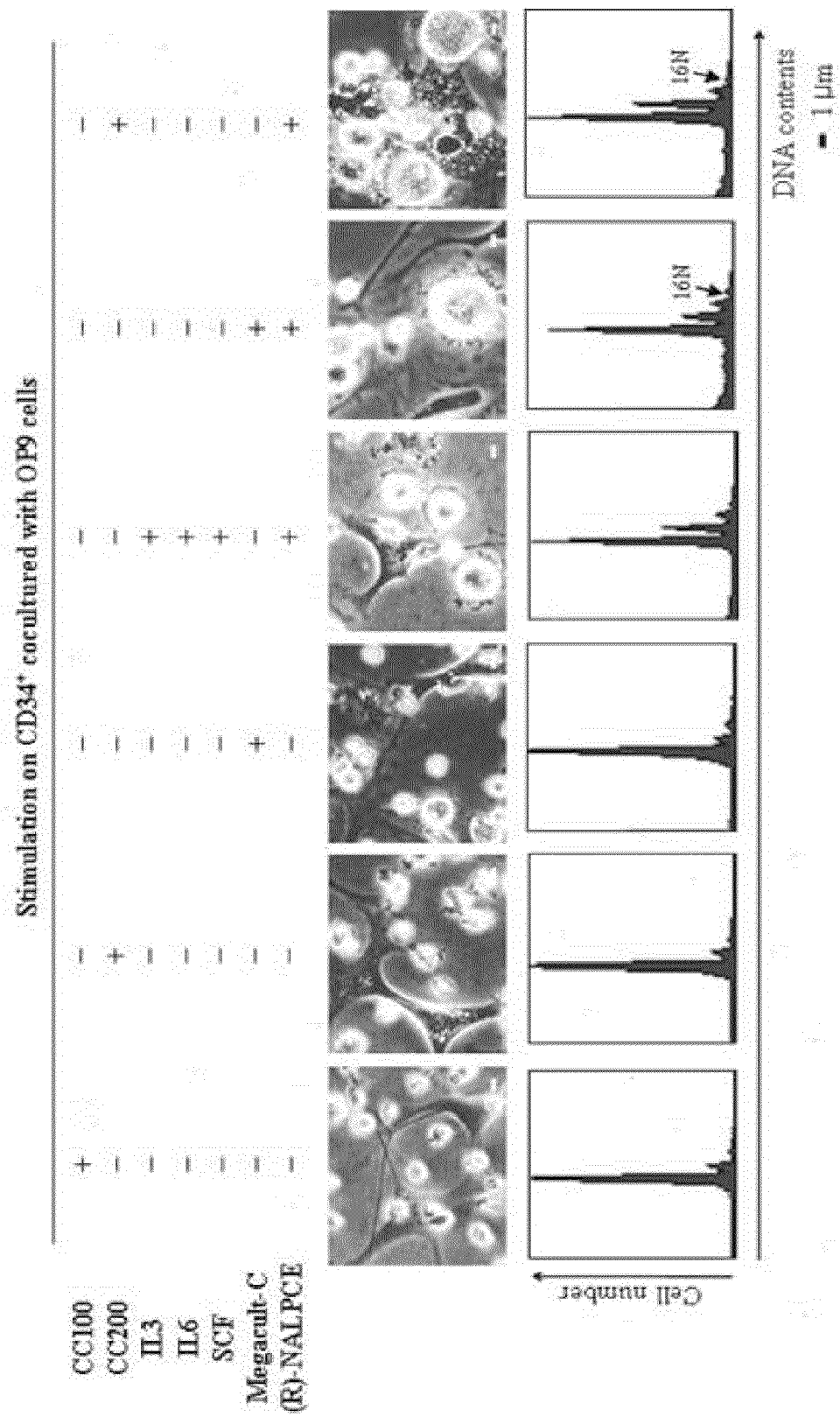
FIG. 1 is images and FACS results showing morphological changes and polyploidization of CD34+ cells.

In accordance with an aspect, the present invention pertains to a method for inducing the differentiation of CD34+ hematopoietic stem cells into megakaryocytes and platelets, comprising the steps of (a) coculturing CD34+ hematopoietic stem cells with stromal cells; and (b) adding the compound of Formula 1.

[Formula 1]

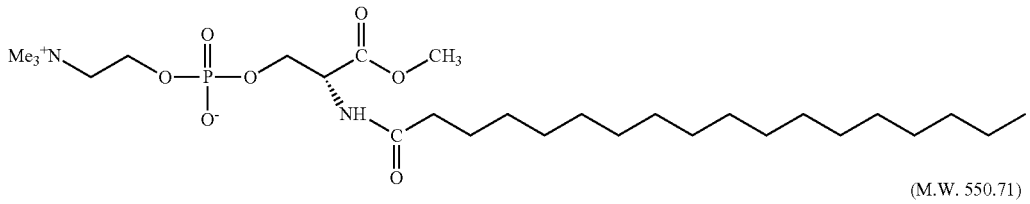

(M.W. 550.71)

Hereinbelow, the method for inducing the differentiation of CD34+ hematopoietic stem cells into megakaryocytes and platelets of the present invention will be described in detail.

In the present invention, step (a) is a step of coculturing CD34+ hematopoietic stem cells with stromal cells, in which CD34+ hematopoietic stem cells are cocultured with stromal cells to facilitate their differentiation into megakaryocytes and platelets.

The term "hematopoietic stem cell", as used herein, refers to a cell having the ability to differentiate into blood cells, such as erythrocyte, leukocyte, and platelet. Hematopoietic stem cell exhibits a unique capacity for self-renewal in an undifferentiated state and differentiation into all types of blood cells by stimulation. The hematopoietic stem cell of the present invention may derived from all animals such as human, monkeys, pigs, horses, cows, sheep, dogs, cats, mice, and rabbits, preferably human, and more preferably human bone marrow, peripheral blood, and umbilical cord blood.

In addition, the hematopoietic stem cell of the present invention has a CD34 positive surface marker, in which 'CD34 surface marker' is a marker for primitive hematopoietic progenitor cells. That is, if a cell has the CD34 surface marker, it expresses a CD34 antigen protein, indicating that the cell is a primitive hematopoietic progenitor. CD34 antigen is a glyocophospoprotein having the molecular weight of 116 kDa, whose genes are located on the long arm of chromosome 1, and expressed in 1-2% of normal bone marrow cells, especially in primary hematopoietic progenitor cells. CD34 positive (also expressed as 'CD34+') hematopoietic stem cells are able to differentiate into various types of blood cells such as erythrocyte, leukocyte, and platelet.

In the present invention, hematopoietic stem cells having the CD34 positive surface marker are preferably CD34+ cells that are directly isolated from bone marrow or umbilical cord blood, and may be also commercially available human CD34+ stem cells. Examples of the method for isolating CD34+ hematopoietic stem cells from bone marrow or umbilical cord blood may include the known methods for obtaining multipotent stem cells expressing desired surface antigens from the obtained stem cell broth, such as FACS method using the flow cytometry with sorting function (Int. Immunol., 10(3):275, 1998), a method using magnetic beads, and a panning method using the antigens specifically recognizing multipotent stem cells (J. Immunol., 141(8):2797, 1998), for example, MACS magnetobead separation system (Miltenyi Biotecl Bergisch-Gladbach, Germany), but are not limited thereto.

In the present invention, 'stromal cell' refers to a cell that lacks M-CSF (Macrophage-Colony stimulating factor) and CSF-1 (Colony Stimulating factor-1), which are needed for differentiating embryonic stem cells into cells of various lineages, but express hematopoietic factors, such as SCF (Stem Cell Factor) and IL-6. Example thereof includes OP9 stromal cells derived from new born calvaria of the F2(C57BL/6xC3H)-op/op.

The term 'coculture', as used herein, refers to the growth of distinct cell types in a combined culture. In the present invention, it is preferable that the stromal cell is cultured as a monolayer in culture media supplemented with FBS, and then the CD34$^+$ hematopoietic stem cells are seeded upper confluent stromal cells. At this time, it is preferable that the stromal cells are aliquoted into culture plate and cultured as a monolayer. For example, the stromal cells are aliquoted into a 40 mm-well, that is, OP9 cells at a density of $1\times10^3$ to $1\times10^7$/well, and preferably $1\times10^4$ to $1\times10^6$/well into a 6-well plate. The OP9 stromal cells are cultured for 18 to 36 hr, and preferably 20 to 28, so that the cells are grown to confluency and create a monolayer on the bottom of the culture plate.

In the present invention, CD34+ hematopoietic stem cells are cultured in media which assure the growth and survival of stem cells in vitro, and which may include all of the pertinent media typically used in the art. Examples thereof include, but are not limited to, DMEM (Dulbecco's Modified Eagle's Medium), MEM (Minimal essential Medium), BME (Basal Medium Eagle), RPMI, F-10, F-12, αMEM (α Minimal essential Medium), GMEM (Glasgow's Minimal essential Medium), CCMM (cell culture minimum medium), Iscove's Modified Dulbecco's Medium and Stemspan™ H3000 medium, and the culture media and conditions depend on the kind of cells.

In a specific embodiment of the present invention, the bone marrow stromal cell line OP9 is aliquoted into a 6-well culture plate at a density of $1\times10^5$ per well, and cultured in a-MEM supplemented with FBS, penicillin/streptomycin, and sodium bicarbonate for 24 hrs. When a monolayer is observed, the CD34+ hematopoietic stem cell was seeded into each well of plate containing confluent OP9 stromal cells at a density of $3\times10^5$ per well.

Meanwhile, step (b) of the present invention is a step of adding the compound of Formula 1 to the CD34+ hematopoietic stem cell of step (a), so as to induce the differentiation of the CD34+ hematopoietic stem cells into megakaryocytes and platelets.

The compound of Formula 1 of the present invention is N-steroyl-O-phosphocholine-D-serine methyl ester, the synthesis method of which is elucidated in detail in Korean Pat. 10-0398892. The present invention encompasses the compound of Formula 1 and derivatives thereof, as long as they provide the potential to differentiate the CD34+ hematopoietic stem cells into megakaryocytes.

The term "differentiation", as used herein, refers to a process whereby undifferentiated stem cells acquire a more specialized fate. In the present invention, it refers to a process whereby the undifferentiated hematopoietic stem cell, preferably CD34+ hematopoietic stem cell is differentiated to the specialized megakaryocyte and thrombocyte having a platelet-producing capacity.

In the present invention, the compound of Formula 1 is added to the CD34+ hematopoietic stem cells that are cocultured with the stromal cells, and the compound is contained in the culture media at a concentration which does not exert cytotoxicity on the CD34+ hematopoietic stem cell but induces the megakaryocytic differentiation, preferably 10 to 60 μg/ml, and more preferably 50 μg/ml, but is not limited thereto.

Further, in step (b), the known materials which effectively differentiate hematopoietic stem cells into megakaryocytes and platelets may be further added, in addition to the compound of Formula 1. Examples thereof may include cytokines such as interleukin-3 (IL-3), IL-6, and IL-11, leukemia inhibitory factor (LIF), erythropoietin (EPO), SCF (stem cell factor), thrombopoietin (TPO), and megacult-C.

The cells that are differentiated from CD34+ hematopoietic stem cells by steps (a) and (b) of the present invention have physiological or immunological properties of megakaryocyte, preferably an increased expression level of megakaryocyte-specific markers. For example, the cells are characterized by an increased expression level of megakaryocyte-specific receptor, CD41 or CD61.

In addition, the cells induced for megakaryocytic differentiation by the method of the present invention have a platelet-releasing activity. For example, the cells are characterized in that they have the polyploid nuclei through endomitosis and their size is increased. In addition, the cells have demarcation channels within which platelets are held. With the advance of maturation, the nuclei undergo further lobulation and concentration while the cytoplasm increases in volume and is further acidophilic and granulated. In the most mature megakaryocytic lineage cells, platelets are released from cell verges.

In a specific embodiment of the present invention, the CD34+ hematopoietic stem cells were treated with the compound of Formula 1 and hematopoietic stem cell differentiation inducers, CC100, CC200, IL-3, IL-6, TPO and SCF, so as to induce the differentiation. As a result, in the cells treated with the compound of Formula 1, it was observed that the cytoplasm increased in volume and the cell size was also increased to be morphologically and functionally similar to megakaryocytes. In addition, an increased polyploidization through endomitosis was observed, which is a characteristic of the megakaryocyte having a platelet-releasing activity, resulting in high nucleus number.

Further, the CD34+ hematopoietic stem cells were treated with the compound of Formula 1 and hematopoietic stem cell differentiation inducers, CC200 and Megacult-C singly or in a mixture, so as to induce the differentiation. As a result, it was found that when the cells were treated with a mixture of the compound of Formula 1 and CC200 or megacult-C, the expression of the megakaryocyte-specific marker CD41 or CD61 was increased, as compared to the single treatment of CC200 or megacult-C. These results indicate that the compound of Formula 1 promotes the potential of the CD34+ hematopoietic stem cell to differentiate into megakaryocytes, leading to effective induction of the differentiation into megakaryocyte and platelet.

In accordance with another aspect, the present invention relates to a composition for inducing the differentiation of CD34+ hematopoietic stem cells into megakaryocytes and platelets, comprising the compound of Formula 1 as an effective ingredient.

The composition for inducing the differentiation into megakaryocytes and platelets of the present invention provides the CD34+ hematopoietic stem cells with a potential to differentiate into megakaryocyte and platelet. Thus, when it is administered to the patients with a low platelet count by chemotherapy or radiotherapy, the differentiation of hematopoietic stem cells into platelets can be promoted. Accordingly, the composition can be used as a pharmaceutical composition for the treatment of thrombocytopenia.

In accordance with still another aspect, the present invention relates to a therapeutic agent for thrombocytopenia, comprising the megakaryocytes and platelets that are obtained by the differentiation induction methods comprising the steps (a) and (b).

The megakaryocytes having a platelet-producing ability, which are obtained by the method of the present invention, and platelets produced therefrom can be used as a cell therapy for the treatment of thrombocytopenia. As used herein, the cell therapy encompasses a pharmaceutical composition comprising megakaryocytes and platelets that are obtained by the method of the present invention, and may be provided in a form of pharmaceutical formulation comprising the composition.

In the present invention, examples of the diseases associated with the reduction of thrombocyte production include thrombocytopenia that results from the reduction of thrombocyte production due to leukemia, metastatic cancer, blood and bone marrow diseases (e.g., aplitic anemia, primary myelofibrosis, myelodysplasia, etc.), vitamin 12 or folate deficiency, and/or bone marrow injury; the destruction of thrombocytes due to sepsis, valvular heart surgery, systemic lupus erythematosus (S.L.E.), lymphoma, chronic lymphocytic leukemia, infectious diseases (e.g., infectious mononucleosis, etc.), and/or drugs (e.g., penicillin, cephalosporin, thiazide, etc.); or abnormal thrombocyte distribution due to tumor- or portal hypertension-caused splenomegaly.

In accordance with still another aspect, the present invention relates to a composition for detecting the differentiation of hematopoietic stem cells into megakaryocytes and platelets, comprising an agent measuring expression level of a gene that is selected from the group consisting of KLF2 (Kiruppel-like factor2), LOC138255 (OTTHUMP00000021439), GDF15 (growth differentiation factor 15) and INHBE (inhibin, betaE).

The term "human bone marrow-derived leukemia cell line", as used herein, means a transformed cell line derived from hematopoietic stem cells. This cell line can be differentiated into monocytes, neutrophils, eosinophils, erythrocytes, macrophages, megakaryocytes, and thrombocytes. In a specific embodiment of the present invention, the human bone marrow-derived leukemia cell line is K562 cell. "K562 cell" is a CML-derived cell line, originally established from a patient with chronic myelogenous leukemia in the terminal blast crisis stage, and a potential to differentiate into various blood cells, such as erythrocyte, megakaryocyte, and neutrophils, like hematopoietic stem cells.

The term "marker for detecting the differentiation of hematopoietic stem cells into megakaryocytes and platelets", as used herein, means an organic biomolecule, of which expression shows a significant difference between the differentiation-induced experimental group and the control group. With respect to the objects of the present invention, the marker of the present invention is significantly increased in the differentiated cells, thereby being used as a gene marker for the detection of differentiation.

Examples of the gene used as the marker of the present invention include genes of which quantities are significantly increased in differentiated cells relative to undifferentiated cells, preferably KLF2 (Kiruppel-like factor2), LOC138255 (OTTHUMP00000021439), GDF15 (growth differentiation factor 15) and INHBE (inhibin, betaE).

In the present invention, expression patterns of the genes that are involved in the differentiation of hematopoietic stem cells into megakaryocytes and platelets were analyzed using an oligonucleotide array to select five genes, of which expressions were increased 10-fold in differentiated megakaryocytes than undifferentiated hematopoietic stem cells. Their expression patterns during the differentiation were analyzed, and the differentiation was found to be suppressed by shRNAs of the gene. Thus, KLF, LOC, GDF15, and INHBE genes can be used as a marker capable of detecting the differentiation of hematopoietic stem cells into megakaryocytes and platelets.

Gene information of the marker genes used in the present invention is available through the National Institutes of Health (NIH) GenBank, specifically KLF2 (Kruppel-like factor, NM_016270.2), LOC138255 (OTTHUMP00000021439, NM_001010940.1), GDF15 (growth differentiation factor 15, NM_004864.1), and INHBE (inhibin, betaE, NM_031479.3). The marker genes used in the present invention encompass functional equivalents to the nucleic acid molecules constituting these genes. Specifically, the marker genes of the present invention also include a functional equivalent that exerts activity functionally identical to the marker genes. The functional equivalent, which includes a functional fragment of the polynucleotide, may include variants in which one or more nucleotide bases are altered by substitutions, deletions, insertions or combinations thereof.

In accordance with a specific embodiment of the present invention, a genechip analysis was performed using an oligonucleotide array from Macrogen, in order to understand the genetic events of (R)-NALPCE during megakaryocytic development when the leukemia cells derived from human bone marrow were treated with (R)-MALPCE to induce the differentiation into megakaryocytes and platelets (see Korean Patent Publication No. 10-0688261). From analyzed data, total 67 genes were assigned, of which quantities are significantly increased in differentiated megakaryocytes relative to undifferentiated hematopoietic stem cells. The functional categories included transcription factor receptor, miscellaneous function, select calcium binding protein, phosphatase, signaling molecule, select regulatory factor, protease, nucleic acid binding, cytoskeleton protein, kinase, cell adhesion molecule, transferase, synthase, hydrolase defence/immunity and molecular function unclassified. Among these genes, 5 genes by (R)-NALPCE increase more 10-fold such as KLF2, LOC138255, GDF15, and INHBE were selected.

The term "agent measuring the gene expression level", as used herein, means a molecule that is used for the detection of the marker genes in the differentiation into megakaryocytes and platelets. In the present invention, the agent measuring the gene expression level is not specifically limited, as long as it is able to measure expression levels of the marker genes at gene or protein level, preferably primers being specific to the marker genes or antibodies being specific to the proteins encoded by the marker genes. Specifically, the agent measuring the gene expression level may be primers for measuring mRNAs of the marker genes or antibodies for measuring the quantities of the marker proteins.

In the present invention, gene level analysis may be performed by the known method that is generally used for the measurement of gene expression level, preferably PCR using primers that are synthesized on the basis of nucleic acid sequences of the marker genes, or as probes in hybridization. Alternatively, a Northern blotting technique (Peter B. Kaufina et al., Molecular and Cellular Methods in Biology and Medicine) is useful for gene level analysis.

The term "primer", as used herein, refers to a single-stranded oligonucleotide capable of acting as a point of initiation of DNA synthesis under conditions (e.g., in the presence of four different nucleoside triphosphates (ATP, GTP, CTP, TTP) and DNA polymerase) in an appropriate buffer and at a suitable temperature. The appropriate length of a primer depends on the intended use of the primer but typically ranges from 10~100, preferably 10~50, and more preferably 10~30 nucleotides. Short primer molecules generally require cooler temperatures to form sufficiently stable hybrid complexes with the template. A primer need not reflect the exact sequence of the template nucleic acid, but must be sufficiently complementary to hybridize with the template. In a specific embodiment, primers to be used in the present invention may be a pair of primers being specific to each marker gene (i.e., KLF2 (SEQ ID NO. 1 and SEQ ID NO. 2), LOC138255 (SEQ ID NO. 3 and SEQ ID NO. 4), GDF15 (SEQ ID NO. 5 and SEQ ID NO. 6), and INHBE (SEQ ID NO. 7 and SEQ ID NO. 8)). In a specific embodiment of the present invention, expression pattern of each marker gene was analyzed during the differentiation of hematopoietic stem cells into megakaryocytes and platelets by RNeasy mini kit using a pair of primers being specific to each marker gene. It was found that the genes were substantially expressed at 12 hrs after induction of differentiation.

In addition, protein level analysis may be quantitatively or qualitatively performed by immunoassay using antibodies against proteins encoded by the marker genes (immunoassay, e.g., RadioImmunoassay RadioImmunoprecipitation Assay Enzyme-Linked ImmunoSorbent Assay, dot blot analysis, Western blot, inhibitory or competitive analysis and sandwich analysis) (Enzyme Immunoassay, E. T. Maggio, ed., CRC Press, Boca Raton, Fla., 1980).

The term "antibody", as used herein, refers to a specific protein molecule that indicates an antigenic region. With respect to the objects of the present invention, an antibody binds specifically to proteins that are encoded by the marker genes of the present invention, KLF2 (Kruppel-like factor2), LOC138255 (OTTHUMP00000021439), GDF15 (growth differentiation factor 15) and INHBE (inhibin, betaE), and includes all of polyclonal antibodies and monoclonal antibodies. Antibody production using the marker proteins identified as described above may be easily carried out using techniques widely known in the art.

Polyclonal antibodies may be produced by a method widely known in the art, which includes injecting the megakaryocytic differentiation marker protein antigen into an animal and collecting blood samples from the animal to obtain serum containing antibodies. Such polyclonal antibodies may be prepared from a certain animal host, such as goats, rabbits, sheep, monkeys, horses, pigs, cows and dogs.

Monoclonal antibodies may be prepared by a method widely known in the art, such as a fusion method (see, Kohler and Milstein (1976) *European Journal of Immunology* 6:511-519). The hybridoma method employs cells from an immunologically suitable host animal injected with a megakaryocytic differentiation marker protein as an antigen, such as mice, and a cancer or myeloma cell line as another group. Cells of the two groups are fused with each other by a method widely known in the art, for example, using polyethylene glycol, and antibody-producing cells are proliferated by a standard tissue culture method. After uniform cell colonies are obtained by subcloning using a limited dilution technique, hybridomas capable of producing an antibody specific for the marker protein are cultivated in large scale in vitro or in vivo according to a standard technique. Monoclonal antibodies produced by the hybridomas may be used in an unpurified form, but are preferably used after being highly purified by a method widely known in the art so as to obtain best results.

Antibodies used in the present invention may be purified using gel electrophoresis, dialysis, salting out, ion exchange chromatography, affinity chromatography, and the like.

The antibodies used in the detection of megakaryocytic differentiation marker of the present invention include complete forms having two full-length light chains and two full-length heavy chains, as well as functional fragments of antibody molecules. The functional fragments of antibody molecules refer to fragments retaining at least an antigen-binding function, and include Fab, F(ab'), F(ab')2, Fv or the like.

In accordance with still another aspect, the present invention relates to a kit for detecting the differentiation marker from hematopoietic stem cells into megakaryocytes and platelets, comprising the composition for detecting a megakaryocytic differentiation marker.

The kit for detecting the differentiation marker of the present invention may include a primer or an antibody selectively recognizing the marker protein of which expression is increased or decreased during the megakaryocytic differentiation, as well as instruments/reagents used in the immunoassay. Examples of the instruments/reagents include suitable carriers, chemiluminophores capable of producing detectable signals, dissolving agents, washing agents, buffering agents or stabilizing agents, but are not limited thereto. If the chemiluminophore is an enzyme, the instruments/reagents may additionally include substrates allowing the measurement of the activity of the enzyme and reagents terminating the enzymatic reaction. Non-limiting suitable carriers include soluble carriers, for example, physiologically acceptable buffer known in the art, e.g., PBS, insoluble carriers, for example, polystyrene, polyethylene, polypropylene, polyester, polyacrylonitrile, fluorine resin, cross-linked dextran, polysaccharides, polymers such as magnetic microparticles made of latex coated with a metal, other paper, glass, metals, agarose, and mixtures thereof.

Non-limiting examples of the kit for detecting the megakaryocytic differentiation marker of the present invention include ELISA plates, dip-stick devices, immunochromatography test strips and radial partition immunoassay devices, and flow-through devices, preferably microarrays. Further, if antibodies against megakaryocytic differentiation marker proteins are provided in a protein chip immobilizing with a plurality of proteins, antigen-antibody complex formation against two or more antibodies is observed. Thus, it is more advantageous in the detection of differentiation into megakaryocytes and platelets.

In accordance with still another aspect, the present invention relates to a method for detecting the differentiation of hematopoietic stem cells into megakaryocytes and platelets by examining expression levels of the marker genes. Expression levels of the marker genes of the present invention may be performed by the known method without limitations, preferably Reverse Transcription Polymerase Chain Reaction (RT-PCR) to measure gene expression level or Western blotting method to measure protein expression level.

In accordance with a specific aspect, the method for detecting the differentiation of hematopoietic stem cells into megakaryocytes and platelets at gene level may include the steps of (a) obtaining a nucleic acid sample from hematopoietic stem cells; (b) measuring expression level of a gene selected from the group consisting of KLF2 (Kruppel-like factor2), LOC138255 (OTTHUMP00000021439), GDF15 (growth differentiation factor 15) and INHBE (inhibin, betaE) in the nucleic acid sample; and (c) determining whether the hematopoietic stem cells are differentiated into megakaryocytes on the basis of the overexpression of the genes of step (b).

Specifically, the gene expression level of step (b) is measured as follows. RT-PCR and electrophoresis are performed using the nucleic acid sample obtained from the hematopoietic stem cells, of which differentiation into megakaryocytes is induced, and the primers specific to the marker genes. Then, mRNA expression levels of the marker genes are measured to detect the differentiation.

Further, the method for detecting the differentiation of hematopoietic stem cells into megakaryocytes and platelets at protein level may include the steps of contacting the hematopoietic stem cells with antibodies against the proteins encoded by the marker genes to form an antigen-antibody complex, and comparing the antigen-antibody complex formation with that of control group.

The term "antigen-antibody complexes", as used herein, refers to binding products of a megakaryocytic differentiation marker protein to an antibody specific thereto. The amount of antigen-antibody complex is compared between in the differentiation-induced group and control group, and the differentiation may be detected by measuring a difference in the amount of antigen-antibody complex.

The amount of formed antigen-antibody complexes may be quantitatively determined by measuring the signal size of a detection label. Such a detection label may be selected from the group consisting of enzymes, fluorescent substances, ligands, luminescent substances, microparticles, redox molecules and radioactive isotopes, but the present invention is not limited to the examples. Examples of enzymes available as detection labels include, but are not limited to, β-glucuronidase, β-D-glucosidase, β-D-galactosidase, urase, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, and β-latamase. Examples of the fluorescent substances include, but are not limited to, fluorescin, isothiocyanate, rhodamine, phycoerythrin, phycocyanin, allophycocyanin, o-phthaldehyde and fluorescamin. Examples of the ligands include, but are not limited to, biotin derivatives. Examples of luminescent substances include, but are not limited to, acridinium esters, luciferin and luciferase. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, K4W(CN)8, [Os(bpy)3]2$^+$, [RU(bpy)3]2$^+$ and [MO(CN)8]4$^-$. Examples of the radioactive isotopes include, but are not limited to, $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

The formation of the antigen-antibody complexes may be detected by a method, but not limited to, selected from the group consisting of a colorimetric method, an electrochemical method, a fluorimetric method, luminometry, a particle counting method, visual assessment and a scintillation counting method. Preferably, the antigen-antibody complexes may be detected by western blotting or ELISA (enzyme-linked immunosorbent assay).

In accordance with still another aspect, the present invention relates to a method for regulating the differentiation of hematopoietic stem cells into megakaryocytes and platelets by increasing or decreasing expression of the gene selected from the group consisting of KLF2 (Kiruppel-like factor2), LOC138255 (OTTHUMP00000021439), GDF15 (growth differentiation factor 15) and INHBE (inhibin, betaE).

In the present invention, to increase the gene expression level for the effective induction of the differentiation into megakaryocytes and platelets, the various methods known in the art may be employed. Preferably, vectors harboring the genes are constructed, and transfected into cells to increase the gene expression level.

Further, in the present invention, to inhibit the differentiation into megakaryocytes and platelets, the gene expression level may be decreased by the methods known in the art, which are able to remove gene function by gene deletion or alteration. Preferably, shRNAs (small hairpin RNA) against the genes are constructed, and transfected into cells to decrease the gene expression level.

In a specific embodiment of the present invention, when shRNAs against the marker genes are constructed, and transfected into the hematopoietic stem cells to suppress gene expression, a unique feature of megakaryocytes, polyploidization was inhibited in the hematopoietic stem cells, of which differentiation into megakaryocytes was induced, and their distinct morphological changes were not observed. In addition, the differentiation of K562 cells that were transfected with shRNA against the marker gene was induced, and then the known megakaryocyte-specific marker, CD41 and CD61 were analyzed using anti-CD41/PECY5 and anti-CD61/Percp. It was observed that the expressions of CD41 and CD61 proteins were inhibited. In addition, the gene expression levels in the K562 cells that were treated with shRNAs against KLF2 and LOC138255 was analyzed by RT-PCR. mRNA expressions of KLF2 and LOC138255 were inhibited, compared to the control group that was not treated with shRNAs.

These results indicate that KLF2, LOC138255, GDF15, and INHBE genes of the present invention substantially regulate the differentiation of hematopoietic stem cells into megakaryocytes and platelets, and the expression levels of these genes are regulated to control the differentiation into megakaryocytes and platelets, thereby being applied to the treatment of platelet-related diseases.

In accordance with still another aspect, the present invention relates to a differentiation regulator for regulating the differentiation of hematopoietic stem cells into megakaryocytes and platelets, comprising one or more of the genes as an effective ingredient.

The term "differentiation regulator", as used herein, refers to a substance capable of regulating the differentiation of hematopoietic stem cells into megakaryocytes and platelets, and refers to a regulator that increases the gene expression levels to effectively induce the differentiation or decreases the gene expression levels to effectively inhibit the differentiation. In the present invention, the differentiation regulator may include a molecule capable of increasing the gene expression levels, preferably a vector capable of overexpressing the genes, and a molecule capable of decreasing the gene expression levels, preferably shRNA against the genes.

In accordance with still another aspect, the present invention relates to a pharmaceutical composition for the treatment of thrombocytopenia, comprising a gene expression- or protein activity-promoting material as an effective ingredient.

The gene expression- or protein activity-promoting material of the present invention may be materials that include the genes so as to amplify the gene expression in a cell, or synthetic or natural compounds, or novel proteins capable of promoting the gene expression or protein activity.

The genes may be introduced into cells using various transfection techniques such as a DNA/DEAE-dextran complex, a DNA/nuclear protein complex, and a DNA/lipid complex, and the genes may be included in a delivery vehicle for efficient introduction into cell. The delivery vehicle is preferably a vector, including viral and non-viral vectors. Examples of the viral vector include a retroviral vector, an adenoviral vector and an adeno-associated viral vector.

Examples of thrombocytopenia-associated diseases that can be treated by targeting the genes of the present invention include, as the above-described, hereditary thrombocytopenia, idiopathic thrombocytopenic purpura, aplastic anemia, myelodysplastic syndrome, acute myelogenous leukemia, and secondary thrombocytopenia.

In accordance with still another aspect, the present invention relates to a pharmaceutical composition for the treatment of thrombocythemia, comprising a gene expression- or protein activity-inhibitor as an effective ingredient. Examples of the gene expression inhibitor may preferably include antisense oligonucleotides, RNAis, siRNAs, or shRNAs, as well as any material capable of inhibiting expression of a gene of interest, such as low-molecular weight compounds, natural products, bioactive proteins, in vivo proteins, novel proteins, and synthetic and naturally-occurring chemicals. Therefore, it is possible to use compounds known as the inhibitor of the aforementioned gene in the art, and materials identified by a screening method using the same gene.

The antisense oligonucleotide against the genes of the present invention has been successfully employed to achieve gene-specific inhibition both in vivo and in vitro. The antisense oligonucleotide is a short synthetic DNA strand (or DNA analog) which is antisense (or complementary) to a certain DNA or RNA target. The antisense oligonucleotide is proposed to prevent expression of the protein encoded by a DNA or RNA target. For this purpose, the antisense oligonucleotide binds to the target to thereby halt the protein expression at a transcription, translation or splicing stage. The antisense oligonucleotides include double or single stranded DNA, double or single stranded RNA, DNA/RNA hybrids, DNA and RNA analogs and bases, and sugar or back bone modified oligonucleotides. To increase stability by enhancing resistance to nuclease, the oligonucleotide may be modified by the method known in the art. The modification method is known in the art, and includes modification in the oligonucleotide backbone and modification in sugar moiety or base, but is not limited thereto.

The siRNAs against the genes of the present invention are able to degrade the genes in a cell, so as to inhibit the gene expression, in which the siRNAs may be chemically modified to confer resistance to nuclease degradation. Since siRNA forms a double stranded structure, it is more stable than single stranded ribonucleic acid or antisense oligonucleotide, but rapidly degraded by in vivo nuclease. Thus, its degradation rate may be reduced by chemical modification. A method frequently used for siRNA modification is boranophosphate or phosphorothioate modification, which forms stable linkage between nucleosides of siRNA to confer resistance to nuclease degradation.

In addition, the shRNAs against the genes of the present invention are able to degrade the genes in a cell, so as to inhibit the gene expression, like siRNAs. The shRNA may be synthesized on the basis of siRNA sequence, and it has a short hair pin structure. The shRNA (short hairpin RNA) expressed in lentivirus and adenovirus is recognized and cleaved by Dicer to form siRNA, resulting in an RNAi effect. The shRNA is able to exert long-term RNAi effect relative to siRNA.

Further, the pharmaceutical composition for the treatment of thrombocythemia of the present invention may include a safe and efficient delivery vehicle so as to increase the transfer efficiency of siRNA or shRNA.

In the present invention, the delivery vehicle for delivering the siRNA or shRNA into a cell is preferably a vector. Examples of the viral vector include a retroviral vector, an adenoviral vector, and an adeno-associated viral vector. These viral vectors are advantageous in the delivery of ribonucleic acid into a cell, but problematic in terms of safety, including recombination into active virus in vivo, induction of immune response, and random integration into the host chromosome. Non-viral vectors are advantageous over viral vectors in that toxicity and immune response are low, repeated administration is possible, complex formation with ribonucleic acid is simple, and large-scale production is easy. In addition, the non-viral vector may be conjugated with ligands specific to a target cell or tissue for selective delivery of nucleic acids into target cells. Examples of the non-viral vector may include various formulations such as liposomes, cationic polymers, micelles, emulsions, and nanoparticles. The delivery vehicle is able to enhance the transfer efficiency of desired nucleic acid into any animal cell, depending on the intended use.

Further, the inhibitor decreasing expression of the protein encoded by the gene of the present invention may be an antibody, including monoclonal antibody, polyclonal antibody, chimeric antibody, and humanized antibody. Monoclonal antibodies against the proteins may be prepared by any conventional method for production of monoclonal antibodies known in the art or otherwise may be commercially available. Alternatively, instead of monoclonal antibodies, it may also be possible to use polyclonal antibodies which recognize the aforesaid protein. These polyclonal antibodies may be obtained by any conventional method for production of antiserum known in the art.

Examples of the targeted diseases that is associated with thrombocythemia include essential thrombocythemia (ET), chronic myelogenous (CML), polycythemia vera (PV), agnogenic mteloidmetaplasia (AMM), and sickle cell anemia (SCA).

The pharmaceutical composition for the treatment of thrombocytopenia or thrombocythemia of the present invention may further include pharmaceutically acceptable carriers, in addition to the effective ingredients. Examples of pharmaceutically acceptable carriers include one or more of water, saline, phosphate buffered saline, dextrose, glycerol, ethanol and the like, as well as combinations thereof. The composition may be formulated to provide a rapid release or a sustained or delayed release of the active ingredient after administration. In addition, if the effective ingredient is an antibody, the pharmaceutically acceptable carriers may further include minor amounts of auxiliary substances such as wetting or emulsifying agents, preservatives or buffers, which enhance the shelf life or the effectiveness of binding protein.

Further, the pharmaceutical composition may include pharmaceutically suitable and physiologically acceptable additives such as excipient, disintegrating agent, sweetener, binder, coating agent, blowing agent, lubricant, glidant, solublizer, in addition to the above ingredients.

Further, the composition of the present invention may further include one or more pharmaceutically acceptable carriers to be formulated appropriately for administration, in addition to the above active ingredients. In order to formulate as liquid formulation, the present composition may include pharmaceutically acceptable carriers which have biocompatibility and are sterilized, for example, saline, sterilized water, Ringer's solution, buffered saline, albumin injection solution, dextrose solution, malto dextrin solution, glycerol, ethanol, and mixture thereof. If necessary, other common additives such as antioxidant, buffer, bacteriostatic agent, etc. may be added to the composition. Also, by further adding a diluent, a dispersing agent, a surfactant, a binder or a lubricant, the composition may be formulated to injectable dosage form such as solution, suspension, emulsion, etc., pill, capsule, granule, or tablet.

The pharmaceutical composition of the present invention may be prepared in any form such as granule, powder, coated tablet, tablet, capsule, suppository, syrup, juice, suspension, emulsion, drop, or injectable liquid formulation, and sustained release formulation of an active ingredient.

The composition of the present invention may be administered via various routes including intravenous, intra-arterial, intraperitoneal, intramuscular, intra-arterial, intraperitoneal, intrathoracic, transdermal, intranasal, inhalation, local, intrarectal, oral, intraopthalmic, or intradermal, according to conventional administration methods.

In accordance with still another aspect, the present invention relates to a method for treating thrombocytopenia or thrombocythemia, comprising the steps of administering to a subject in need thereof a therapeutically effective amount of the pharmaceutical composition.

The term "therapeutically effective amount" as used herein means the amount of a compound that, when administered to a subject for treating a state, disorder or condition, is sufficient to effect such treatment. The therapeutically effective amount varies depending on various factors such as the kind of diseases, the severity of diseases, the content of active ingredient, the content and kind of other ingredients, the type of formulation, the age, body weight, health status, gender, and diet of a patient, administration time, administration route, the secretion ratio of composition, treatment period, and other co-administrated drug.

In accordance with still another aspect, the present invention relates to a method for screening a candidate compound that regulates the differentiation of hematopoietic stem cells into megakaryocytes and platelets, comprising the step of treating the candidate compound that regulates the differentiation of hematopoietic stem cells into megakaryocytes and platelets; and measuring expression level of the marker gene selected from the group consisting of KLF2 (Kruppel-like factor2), LOC138255 (OTTHUMP00000021439), GDF15 (growth differentiation factor 15) and INHBE (inhibin, betaE) in hematopoietic stem cells.

The term "candidate compound that regulates the differentiation into megakaryocytes and platelets", as used herein, means a compound that indirectly or directly inhibits or induces a significant change in expression levels of the marker genes, upon differentiation into megakaryocytes and platelets. The screening method of the present invention can select the compounds capable of regulating the differentiation into megakaryocytes and platelets by measuring changes in expression levels of the megakaryocytic differentiation marker genes in the presence or absence of the candidate compound, in particular, the compounds increasing expression levels of the marker genes. Therefore, compounds that effectively induce the differentiation of hematopoietic stem cells into megakaryocytes can be easily screened.

In addition, a pharmaceutical composition comprising the compound regulating the differentiation of hematopoietic stem cells into megakaryocytes and platelets, which is selected by the above screening method, may be used for the treatment of thrombocytopenia or thrombocythemia.

Hereinafter, the preferred Examples are provided for better understanding. However, these Examples are for illustrative purposes only, and the invention is not intended to be limited by these Examples.

COMPARATIVE EXAMPLE 1

Preparation of compound of Formula 1

1-1. Synthesis of D-Serine Methyl Ester Hydrochloric Acid Salt

A solution of 47.7 mmol of D-serine in 476 ml of methanol was saturated with hydrochloric acid gas and allowed to react at room temperature for 2 hrs. Following the evaporation of the solvent, recrystallization with methanol and ether produced the object compound L-serine methyl ester hydrochloric acid salt (Yield: 99%, m.p.: 163-164° C., $[\alpha]^{25}$ D=−4.3(c 1.8, EtOH)). The structure of the synthesized compound was identified using FTIR, $^1$H-NMR and $^{13}$C-NMR.

FTIR (KBr, cm-1): 3349 O—H peak, 2943 sp3 C—H peak, 1749 ester carbonyl peak $^1$H NMR(CD3 OD): δ 4.07~4.10(1H, t, J=3.9 Hz), 3.38-3.93(2H, m), 3.79(3H, s) methoxy carbon cation (s: singlet, d: doublet, t: triplet, m: multiplet)

$^{13}$C NMR(CD3OD): δ 52.69, 55.10, 59.67, 168.37 carbonyl peak 1-2. Synthesis of N-steroyl-D-serine Methyl Ester The compound (1 eq) synthesized in 1-1 was dissolved in 257 ml of dichloromethane and cooled to 0° C. To this solution were sequentially added N-methyl morpholine (2.1 eq), stearic acid (1.1 eq) and 1-hydroxybenzotriazole (1.1 eq), 1,3-dicyclohexylcarbodiimide (1.1 eq) in that order, and the reaction was conducted for 1 hr, and then for 3 hrs at room temperature. Following the completion of the reaction, the by-product dicyclourea was filtered off in a vacuum and the remaining filtrate was concentrated. The concentrate was purified using column chromatography (dichloromethane:acetone=9:1→7:1) to afford the object compound N-steroyl-D-serine methyl ester (Yield: 88%, m.p.: 82-83° C., $[\alpha]^{25}$ D=−15.7(c 2.0, CHCl3)). The synthesized compound was identified by structural analysis through FTIR, $^1$H-NMR and $^{13}$C-NMR.

FTIR (KBr, cm-1): 3310 O—H peak, 2919 sp3 C—H peak, 1720 ester carbonyl peak, 1650 amide carbonyl peak $^1$H NMR(CDCl3): δ 0.83~0.88(3H, m) stearic acid terminal carbon cation, 1.23(28H, s) hydrocarbon cation, 1.60~1.63(2H, m) carbonyl-β-carbon cation, 2.21~2.28 (2H, t, J=7.6 Hz), 2.52(1H, m) hydroxyl group peak, 3.78(3H, s) methoxy carbon cation, 3.93~3.94 (2H, d, J=3.4 Hz), 4.64~4.70(1H, m), 6.36~6.39(1H, d, J=6.5 Hz) amide nitrogen cation $^{13}$C NMR(CDCl3): δ 14.1 stearic acid terminal carbon, 22.7 hydrocarbon carbon, 25.5 carbonyl-β-carbon, 29.2, 29.3, 29.5, 29.7, 31.9 hydrocarbon, 36.5, 52.8 methoxy carbon, 54.6, 63.7, 171.0 carbonyl peak, 173.8 carbonyl peak

1-3. Synthesis of N-steroyl-O-phosphocholine-D-serine Methyl Ester

A solution of the compound (1 eq) synthesized in 1-2 in 260 ml of tetrahydrofuran was cooled to −10° C. To the solution were added N-diisopropylethylamine (4 eq) and ethylenechlorophosphite (3 eq), followed by reaction for 1 hr. The addition of bromine (3 eq) and reaction for 15 min was conducted before the addition of 86.6 ml of water and reaction for 1 hr at room temperature. The organic layer thus separated was evaporated, followed by recrystallization in dichloromethane and acetone. The precipitate was re-dissolved in 87.5 ml of chloroform/isopropanol/acetonitrile (3:5:5, v/v/v) at 0° C., and 40% aqueous trimethyl amine (3 eq) was added to this solution before reaction for 11 hrs. Purification through column chromatography (dichloromethane:methanol:water=3:1:0→2:1:0.1) afforded the object compound N-steroyl-O-phosphocholine-D-serine methyl ester (Yield: 12%, [α]$^{25}$ D=+8.8(c 2.0, MeOH)). The synthesized compound was identified by structural analysis through $^1$H-NMR and $^{13}$C-NMR.

$^1$H NMR(CDCl3): δ 0.90~0.93 (3H, m) stearic acid terminal carbon cation, 1.31(28H, s) hydrocarbon cation, 1.63~1.65(2H, m) carbonyl-β-carbon cation, 2.27~2.33 (2H, t, J=7.2 Hz), 3.25(9H, s) trimethylamine carbon cation, 3.65~3.67(2H, m), 3.77(3H, s) methoxy peak, 4.15~4.19(1H, m), 4.21~4.28(3H, m), 4.68(1H, m);

$^{13}$C NMR(CDCl3): δ 13.5 stearic acid terminal carbon, 22.8 hydrocarbon carbon, 25.9 carbonyl-β-carbon, 29.3, 29.5, 29.8, 32.1, 35.7, 51.9 methoxy carbon, 53.7, 59.5, 65.1, 66.4, 170.6 carbonyl peak, 175.4 carbonyl peak

EXAMPLE 1

Coculture of OP Cell and CD34+ Hematopoietuc Stem Cell

OP9 stromal cell line was purchased from ATCC (American Type Culture Collection, Rockville, Md.). StemSpan™ H3000 media for culture of the umbilical cord blood-derived CD34+ hematopoietic stem cell and CD34+ cell was purchased from STEMCELL Technologies Inc. (Vancouver, CANADA).

The OP9 stromal cell line was aliquoted into 6-well culture plate at a density of 1×10$^5$/well, and cultured for 24 hrs as a monolayer in a-MEM supplemented with 20% heat-inactivated FBS, 0.5% penicillin/streptomycin and 1.5 g/L sodium bicarbonate. When the OP9 stromal cell line was cultured as a monolayer, the media was replaced with StemSpan™ H3000 for CD34+ hematopoietic stem cell culture. Then, the CD34+ hematopoietic stem cells were aliquoted upper the op cells at a density of 3×10$^5$/well.

EXAMPLE 2

Morphological Change and Polyploidization of Compound of Formula 1-Treated CD34+ Hematopoietic Stem Cell In order to confirm the distinct morphological change of the umbilical cord blood-derived CD34+ hematopoietic stem cell treated with the compound of Formula 1, the cells were treated with the compound of Formula 1 and the known hematopoietic stem cell differentiation inducers, CC100, CC200, IL-3, IL-6, TPO and SCF, so as to investigate morphological changes and polyploidization of the CD34+ hematopoietic stem cell.

The CD34+ hematopoietic stem cells cocultured with OP9 cells through Example 1 were treated with each of the materials. The cells were treated with each of the hematopoietic stem cell differentiation inducers at a following concentration; CC100 (rhFlt-3 ligand 100 ng/ml, SCF 100 ng/ml, IL-3 20 ng/ml, IL-6 20 ng/ml), CC200 (rhTPO 50 ng/ml, rhSCF 50 ng/ml, IL-3 10 ng/ml), Megacult-C (TPO 5 ng/ml, IL-3 1 ng/ml, IL-6 2 ng/ml), IL-3 of 10 ng/ml, IL-6 of 20 ng/ml, SCF of 50 ng/ml, and (R)-NALPCE of 45 μg/ml.

After 8 days, the cells were photographed by Mag. ×200 to examine the morphological changes (FIG. 1).

In addition, polyploidization of the cells was analyzed by FACS (flow cytometer). The cells were harvested and resuspended with 1×PBS containing 0.1% saponin. 10 mg/mL RNAse A and propidium iodide solution were added thereto. Thereafter, the cells were incubated at room temperature for 30 min. The cells were analyzed by FACS caliber flow cytometer and Cell quest software. Results are means±SD (n=3). Similar results were obtained in three independent experiments (FIG. 1).

As shown in FIG. 1, unlike other differentiation inducer-treated cells, the compound of Formula 1-treated cells showed a morphological feature of megakaryocytes, such as an increase in cytoplasmic mass and cell size, as well as a feature of megakaryocytes having a platelet-releasing activity, such as high nucleus number due to polyploidization through endomitosis.

In addition, the compound of Formula 1 was found to promote the megakaryocytic differentiation induced by other differentiation inducers. In particular, it was found that the addition of the compound of Formula 1 more induced megakaryocytic differentiation together with some stimulation such as CC200 or Megacult-C, as compared to each single treatment.

EXAMPLE 3

Differentiation of Compound of Formula 1-Treated CD34+ Hematopoietic Stem Cell into Megakaryocyte and Platelet In order to confirm whether the differentiation of the umbilical cord blood-derived CD34+ hematopoietic stem cells into megakaryocytes and platelets was induced by treatment of the compound of Formula 1, the cells were treated with the compound of Formula 1 and the known hematopoietic stem cell differentiation inducers, CC200 and Megacult-C, singly or in a mixture. Then, expression of megakaryocyte-specific marker, CD41 or CD61 was analyzed.

The CD34+ hematopoietic stem cells cocultured with OP9 cells through Example 1 were treated with each of the hematopoietic stem cell differentiation inducers at a following concentration; CC200 (rhTPO 50 ng/ml, rhSCF 50 ng/ml, IL-3 10 ng/ml), Megacult-C (TPO 5 ng/ml), and (R)-NALPCE 35 ug/ml in culture media.

After 8 days, the culture media were centrifuged (1,000 rpm, 10 min), and the cell pellets thus obtained were washed three times with PBS. The cells were incubated with 20 µl of Fluorescein isothiocyanate (FITC)-conjugated mouse anti-human monoclonal CD41 antibody (DAKOCycomation, Denmark) or 20 µl of Fluorescein isothiocyanate(FITC)-conjugated mouse anti-human monoclonal CD61 antibody (DAKOCycomation, Denmark) in 200 µl of 0.01% bovine serum albumin (BSA)-PBS at 37° C. for 30 min while spinning to realize homogeneous fluorescent staining. After centrifugation (1,000 rpm, 10 min), the cell pellets thus obtained were washed three times with 0.01% bovine serum albumin (BSA) in PBS. Fluorescence was analyzed on a fluorescence-activated cell sorter (FACS Aria) using a Cellquest program. Results are means±SD (n=3). Similar results were obtained in three independent experiments (FIG. 2).

Figure 2:
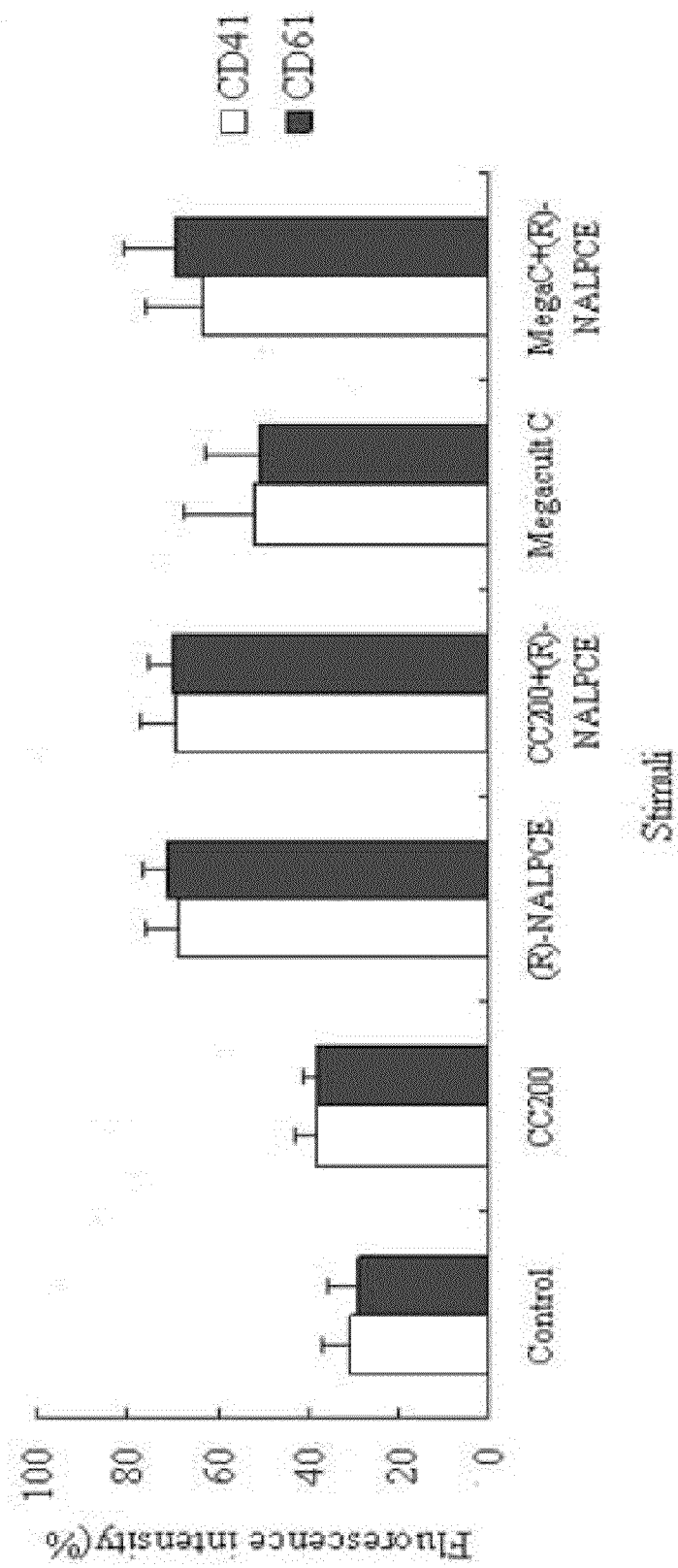
FIG. 2 is the result showing CD41 and CD61 expression levels of CD34+ cells cocultured with OP9 stromal cells, analyzed on a fluorescence-activated cell sorter.

As shown in FIG. 2, the expression level of the megakaryocyte-specific marker, CD41 or CD61 was found to be higher in the cells treated with the compound of Formula 1 than in those treated with CC200 or megacult-C. Also, the expression level of CD41 or CD61 was found to be higher in the cells treated with CC200 or megacult-C together with the compound of Formula 1, as compared to the single treatment of C200 or megacult-C. These results indicate that the compound of Formula 1 promotes the differentiation of CD34+ hematopoietic stem cells into megakaryocytes and platelets.

EXAMPLE 4

K562 Cell (Human Bone Marrow-Derived Leukemia Cell Line) Culture and Induction of Megakaryocytic Differentiation The present inventors have used a human bone marrow-derived leukemia cell line, K562 cell as a hematopoietic stem cell, and purchased K562 cell and OP9 stromal cell from ATCC (American Type Culture Collection, Rockville, Md.).

The OP9 stromal cell line was aliquoted into 6-well culture plate at a density of $1 \times 10^5$/well, and cultured for 24 hrs as a monolayer in a-MEM supplemented with 20% heat-inactivated FBS, 0.5% penicillin/streptomycin and 1.5 g/L sodium bicarbonate. When the OP9 stromal cell line was cultured as a monolayer, the K562 cells were aliquoted upper the OP9 cells at a density of $1 \times 10^5$/well, and cocultured with the OP9 cells. These K562 cells were treated with (R)-NALPLE (see Korean Patent No. 10-0688261) at a concentration of 50 µg/ml to induce megakaryocytic differentiation.

EXAMPLE 5 mRNA Isolation and Oligonucleotide Array mRNAs were extracted from normal K562 cells and compound-treated K562 cells by the method of Example 5. To understand the genetic events during megakaryocytic development, the K562 cells were incubated for 6, 12, 24, 48, 72, 96, and 120 hr with the compound, and mRNAs were extracted from each cell using an RNeasy mini kit (Qiagen, USA). A genechip analysis was performed using 1 µg of RNA and an oligonucleotide array from Macrogen.

From analyzed data, total 67 genes, of which expression levels were increased more than 5-fold in differentiated K562 cells, were assigned. The functional categories included transcription factor, receptor, miscellaneous function, select calcium binding protein, phosphatase, signaling molecule, select regulatory factor, protease, nucleic acid binding, cytoskeleton protein, kinase, cell adhesion molecule, transferase, synthase, hydrolase defense/immunity and molecular function unclassified. Among these genes, selected were 4 genes of which expression levels were increased more 10 fold in differentiated cells, such as KLF2 (Kiruppel-like factor2), LOC138255 (OTTHUMP00000021439), GDF15 (growth differentiation factor 15) and INHBE (inhibin, betaE).

EXAMPLE 6

Measurement of KLF2, LOC138255, GDF15 and INHBE Expression Levels in Cell

To analyze the expression patterns of the selected 4 genes, KLF2, LOC138255, GDF15, and INHBE during megakaryocytic development, RT-PCR was performed to measure the mRNA level in cells.

In order to specifically analyze their expression patterns during megakaryocytic development, the K562 cells were incubated for 6, 12, 24, 48, 72, 96, and 120 hr with the compound ((R)-NALPLE 50 µg/ml). Total cellular RNA was extracted from the K562 cells using an RNeasy mini kit following the manufacturer's instructions using M-MLV Reverse Transcriptase (Promega, Madison, Wis.), and RT-PCR was performed.

Amplification conditions were followed by 20 cycles (for GAPDH) or 25 cycles (for KLF2, LOC138255, GDF15, and INHBE) at 95° C. for 30 seconds, 60° C. for 60 seconds, and 72° C. for 90 seconds. The primers used were the following:

KLF2 forward primer (SEQ ID NO.1): 5'-GCAAGAC-CTACACCAAGAGTTCG-3' reverse primer (SEQ ID NO.2);5'-CATGTGC-CGTTTCATGTGC-3'

LOC138255 forward primer )SEQ ID NO.3); 5'-ATGAG-GAAACAGTGAGCTCC-3' reverse primer )SEQ ID NO. 4);5'-AATCCCACTCTCAT-CATGGCC-3'

GDF15 forward primer 9SEQ ID NO. 5); 5'-ATGGCTCT-CAGATGCTCCTG-3' reverse primer (SEQ ID NO. 6): 5'-AGAGATACG-CAGGGTGCAGGT-3'

INHBE forward primer (SEQ ID NO. 7); 5'-ATGGGGT-TGCACCTGACCAGT-3' reversre primer (SEQ ID NO. 8);5'TTGGTGATGTGGT-GCTCAGC-3'

GARDH forward primer (SEQ ID NO. 9);5'-CTGCAC-CACCAACTGCTTAG-3' reverse primer (SEQ ID NO. 10);5'-AGATCCACGACG-GACACATT-3'

Figure 3:
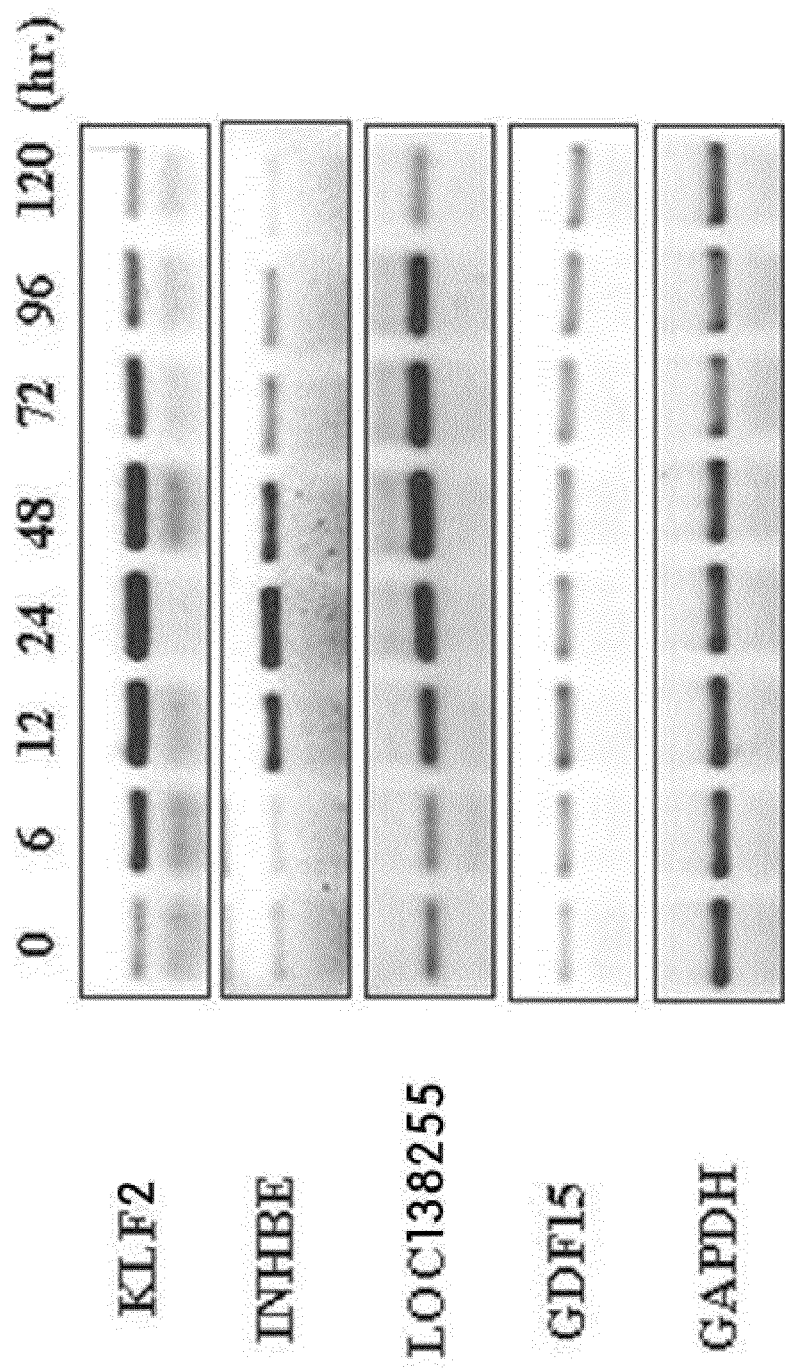
FIG. 3 is the RT-PCR result showing KLF2, LOC138255, GDF15, and INHBE gene expressions in (R)-NALPCE-treated K562 cells during megakaryocytic differentiation.

After PCR reaction, each reaction mixture was analyzed by 1% agarose gel electrophoresis, and the bands were visualized by ethidium bromide staining (FIG. 3).

As a result, it was found that KLF2, LOC138255, GDF15, and INHBE genes were substantially expressed during megakaryocytic development, in particular, markedly expressed at 12 to 96 hr.

EXAMPLE 7

Inhibition of Polyploidization by shRNA and Morphological Changes

To confirm whether the selected genes regulate the differentiation into megakaryocyte and platelets, shRNAs capable of inhibiting expressions of the KLF2, LOC138255, GDF15, and INHBE genes were constructed, and K562 cells were transfected with shRNAs.

Figure 4:
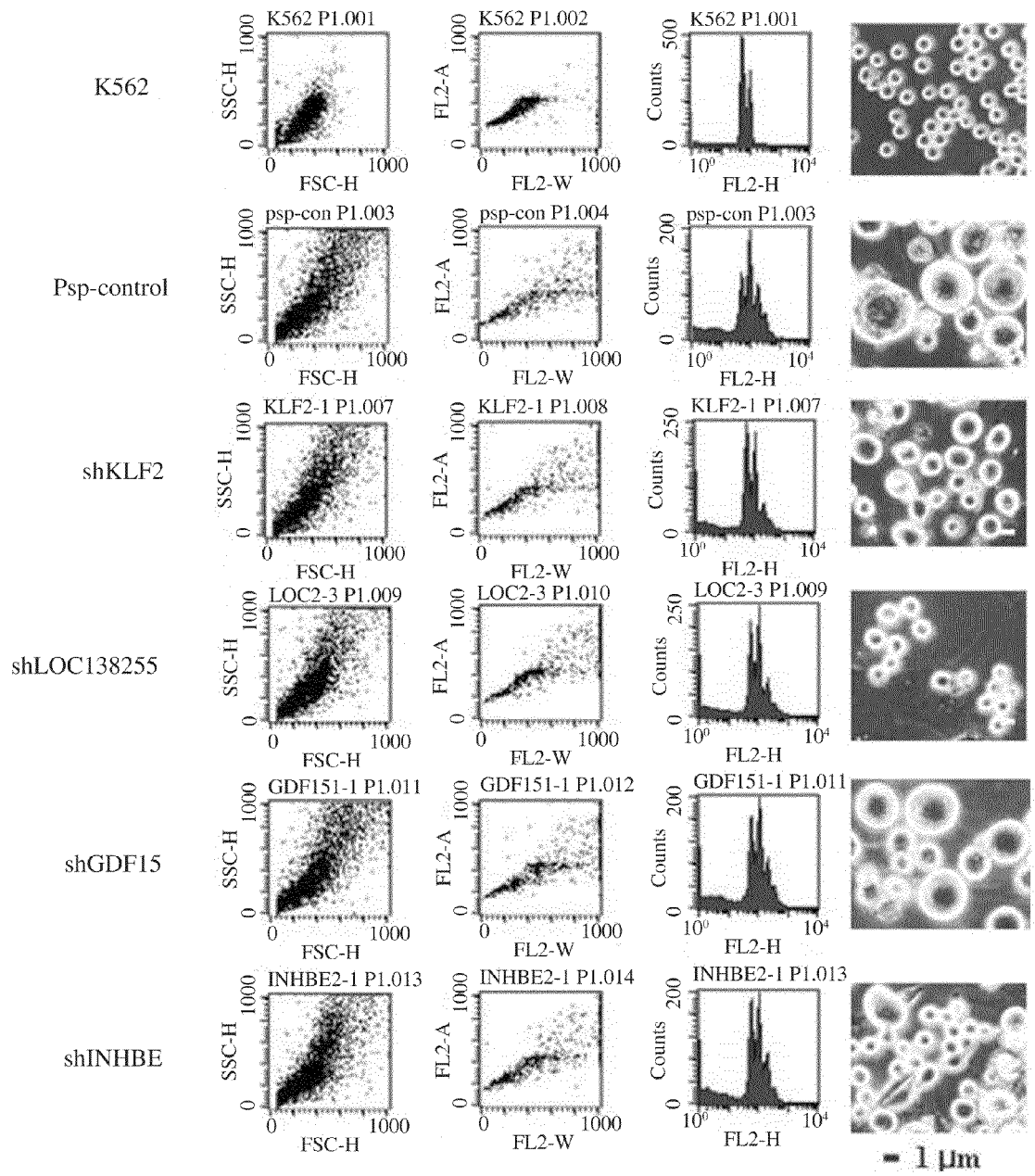
FIG. 4 shows inhibition of polyploidization by shRNA and morphological changes in K562 cells transfected with shRNAs against KLF2, LOC138255, GDF15, and INHBE genes during megakaryocytic differentiation.

The transfected K562 cells were sorted by FACS Aria flow cytometer, and cocultured upper OP9 stromal cells in 50 μg/mL of (R)-NALPCE for 4 days. Then, the cells were analyzed with a fluorescence-activated cell sorter using Cell quest, and photographed by Mag. ×200. Results are means±SD (n=3). Similar results were obtained in three independent experiments (FIG. 4).

As a result, non-transfected K562 cells showed a feature of megakaryocytes having a platelet-releasing activity, such as high nucleus number due to polyploidization through the endomitosis, whereas transfected K562 cells showed decreased nucleus number due to inhibited polyploidization, as compared to the control group. In particular, the cells transfected with shRNAs against KLF2 and LOC138255 genes showed inhibited polyploidization, as well as the similar morphology to normal K562 cells that were treated with no compound.

EXAMPLE 8

Inhibition of Differentiation into Megakaryocyte and Platelet by shRNA

To confirm whether the differentiation of K562 cells into megakaryocytes is inhibited by suppression of the selected gene, K562 cells were transfected with shRNA against each of the KLF2, LOC138255, GDF15, and INHBE genes, and then expression levels of the megakaryocyte-specific markers, CD41 and CD61 were determined.

Figure 5:
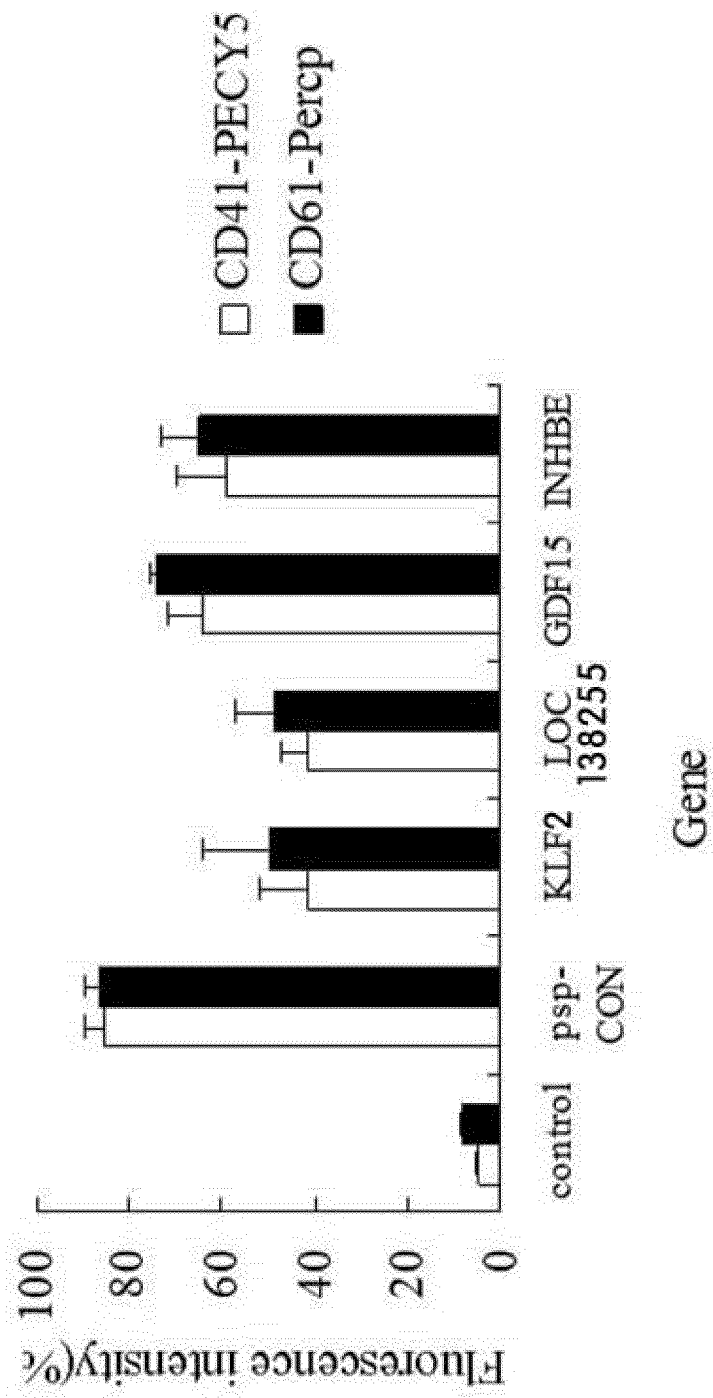
FIG. 5 shows expression of the megakaryocyte-specific markers, CD41 and CD61 in K562 cells transfected with shRNAs against KLF2, LOC138255, GDF15, and INHBE genes during megakaryocytic differentiation.

Transfected K562 cells were cocultured upper OP9 stromal cells in 50 μg/ml (R)-NALPCE. After 4 days, cells were harvested and incubated at 37° C. for 30 min in 200 μl of PBS containing 20 μg/ml anti-CD41/PECY5 and anti-CD61/Percp. Cells were analyzed with a fluorescence-activated cell sorter using Cell quest. Results are means±SD (n=3). Similar results were obtained in three independent experiments (FIG. 5).

As a result, transfected cell showed inhibition of CD41 and CD61 expressions, as compared to non-transfected cells (control group). In particular, the cells that were transfected with shRNAs against the KLF2 and LOC138255 genes showed 50% inhibition of the megakaryocyte-specific markers, CD41 and CD61 expressions, as compared to the control group. These results indicate that the KLF2, LOC138255, GDF15, and INHBE genes are able to directly regulate the differentiation into megakaryocytes and platelets. Furthermore, it can be seen that these genes can be used as a marker for the detection of megakaryocytic differentiation.

EXAMPLE 9

Down-Expression of Gene by shRNA

To confirm down expression of KLF2 and LOC138255 by shRNA thereof, cells were transfected with shRNA, and then RT-PCT was performed using RNA extracted from the cells.

K562 cells were transfected with shKLF2 and shLOC138255, which are shRNAs against KLF2 and LOC138255 genes, using a microporation method. After microporation, the transfected K562 cells were cultured for 4 days. Total RNA was extract from the transfected cells and normal K562 cells, and those genes expression was examined by RT-PCR. Amplification conditions were followed by 20 cycles (for GAPDH) or 25 cycles (for KLF2, LOC138255) at 95° C. for 30 seconds, 60° C. for 60 seconds, and 72° C. for 90 seconds. After PCR reaction, each reaction mixture was analyzed by 1% agarose gel electrophoresis, and the bands were visualized by ethidium bromide staining (FIG. 3).

Figure 6A:
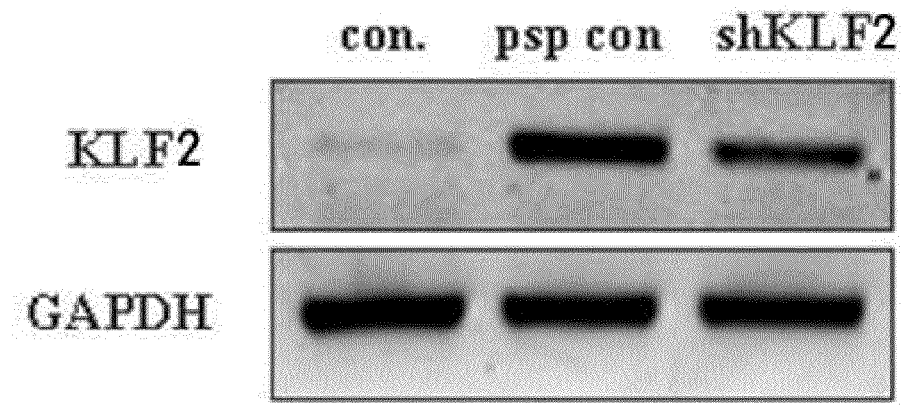
FIG. 6 shows mRNA expression levels of KLF2 and LOC138255 genes in K562 cells transfected with shRNAs against KLF2 and LOC138255 genes during megakaryocytic differentiation.
Figure 6B:
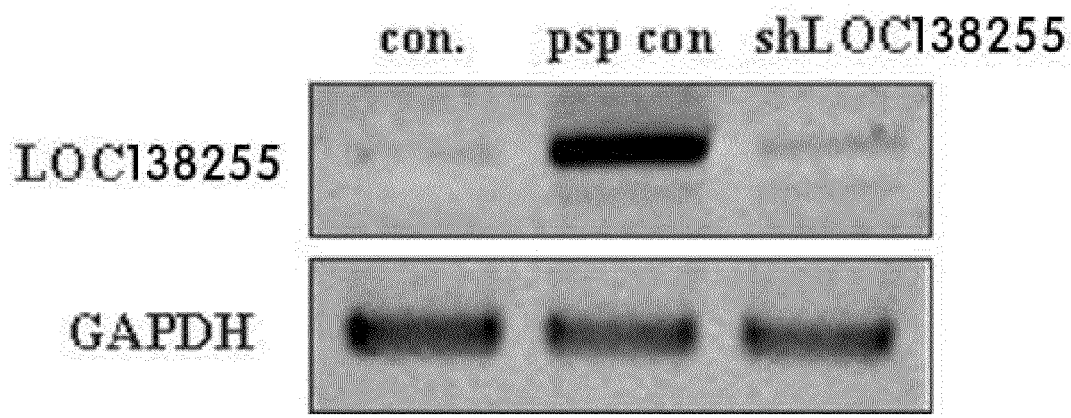

As a result, KLF2 and LOC138255 mRNA expressions were found to be suppressed in the cells transfected with shRNAs against KLF and LOC genes (FIG. 6), indicating that KLF2 and LOC138255 genes may participate in the differentiation of hematopoietic stem cells into megakaryocytes and platelets and their maturation.

Industrial Applicability

The method for inducing the differentiation of CD34+ hematopoietic stem cells into megakaryocytes and platelets using the compound of Formula 1 of the present invention enhances the potential of the CD34+ hematopoietic stem cell to differentiate into megakaryocytes, leading to effective induction of the differentiation into megakaryocyte and platelet. Therefore, the compound of Formula 1 or a pharmaceutical composition formulated using the differentiated megakaryocyte and platelet is useful in the treatment of thrombocytopenia.

Further, the composition for detecting the differentiation into megakaryocytes and platelets according to the present invention is able to easily detect the differentiated megakaryocyte and platelet to be used in the treatment of thrombocytopenia. Thus, the composition can be effectively employed in a kit for detecting the differentiation into megakaryocyte and platelet, and used to screen a candidate compound capable of regulating the differentiation into megakaryocyte and platelet.

Furthermore, the marker genes of the present invention can be used as a novel target gene for the regulation of differentiation into megakaryocyte and platelet and for the development of therapeutic agents for platelet-related diseases.

The invention claimed is:

1. A method for inducing the differentiation of $CD34^+$ hematopoietic stem cells into megakaryocytes and platelets, comprising the steps of (a) coculturing $CD34^+$ hematopoietic stem cells with stromal' cells; and (b) adding the compound of the following Formula 1, wherein expression level of a gene selected from the group consisting of KLF2 (Kruppel-like factor2, NM 016270), LOC138255 (OT-THUMP00000021439, NM 001010940), GDF15 (growth differentiation factor 15, NM 004864) and INHBE (inhibin, betaE, NM 031479) is increased in $CD34^+$ hematopoietic stem cells that are differentiated, relative to undifferentiated $CD34^+$ hematopoietic stem cells.

[Formula 1]

(M.W 550.71).

2. The method according to claim 1, wherein the hematopoietic stem cells are derived from umbilical cord blood, bone marrow, or peripheral blood.

3. The method according to claim 1, wherein step (b) further comprises adding one or more hematopoietic stem cell differentiation inducers selected from the group consisting of interleukin-3 (IL-3), IL-6, IL-11, leukemia inhibitory factor (LIF), erythropoietin (EPO), SCF (stem cell factor), thrombopoietin (TPO), CC 100, CC200, and megacult-C.

* * * * *

UNITED STATES PATENT AND TRADEMARK OFFICE
CERTIFICATE OF CORRECTION

PATENT NO. : 8,137,970 B2
APPLICATION NO. : 12/364341
DATED : March 20, 2012
INVENTOR(S) : Gil-Ja Jhon et al.

It is certified that error appears in the above-identified patent and that said Letters Patent is hereby corrected as shown below:

Title Page, Item (57), Line 12:
"of KLF2 (Kiruppel-like factor2)" should read, --of KLF2 (Kruppel-like factor2)--.

Column 25, Line 32:
"stem cells with stromal' cells;" should read, --stem cells with stromal cells;--.

Column 25, Line 35:
"like factor2, NM 016270)," should read, --like factor2, NM_016270),--.

Column 25, Line 36:
"OTTHUMP00000021439, NM 001010940)," should read, --OTTHUMP00000021439, NM_001010940),--.

Column 25, Line 37:
"differentiation factor 15, NM 004864" should read, --differentiation factor 15, NM_004864--.

Column 25, Line 38:
"betaE, NM 031479" should read, --betaE, NM_031479--.

Column 26, Line 45:
"thrombopoietin (TPO), CC 100," should read, --thrombopoietin (TPO), CC100,--.

Signed and Sealed this
Tenth Day of July, 2012

David J. Kappos
*Director of the United States Patent and Trademark Office*